US007144580B2

(12) United States Patent
Confer et al.

(10) Patent No.: US 7,144,580 B2
(45) Date of Patent: Dec. 5, 2006

(54) ***M. HAEMOLYTICA* OUTER MEMBRANE PROTEIN P1PE AS A VACCINE OR VACCINE COMPONENT AGAINST SHIPPING FEVER**

(75) Inventors: Anthony W. Confer, Stillwater, OK (US); Sahlu Ayalew, Stillwater, OK (US); George L. Murphy, Austin, TX (US); Karamjeet Pandher, Ft. Collins, CO (US)

(73) Assignee: The Board of Regents for Oklahoma State University, Stillwater, OK (US)

( * ) Notice: Subject to any disclaimer, the term of this patent is extended or adjusted under 35 U.S.C. 154(b) by 0 days.

(21) Appl. No.: 11/235,982

(22) Filed: Sep. 27, 2005

(65) Prior Publication Data

US 2006/0078572 A1 Apr. 13, 2006

Related U.S. Application Data

(62) Division of application No. 10/696,544, filed on Oct. 29, 2003, now abandoned.

(60) Provisional application No. 60/422,305, filed on Oct. 30, 2002.

(51) Int. Cl.

| | |
|---|---|
| ***A61K 39/102*** | (2006.01) |
| ***A61K 39/02*** | (2006.01) |
| ***A61K 39/116*** | (2006.01) |
| ***A61K 38/00*** | (2006.01) |
| ***C07K 1/00*** | (2006.01) |

(52) U.S. Cl. .............................. 424/255.1; 424/234.1; 424/190.1; 424/184.1; 424/203.1; 514/2; 530/350; 530/825

(58) Field of Classification Search ............. 424/255.1, 424/234.1, 190.1, 203.1, 184.1; 514/2; 530/350, 530/825

See application file for complete search history.

(56) References Cited

U.S. PATENT DOCUMENTS 5,554,372 A 9/1996 Hunter .................... 424/280.1
2004/0033234 A1 2/2004 Berinstein et al. ....... 424/185.1

FOREIGN PATENT DOCUMENTS

WO WO 2004/041182 A2 5/2004

OTHER PUBLICATIONS

Pandher, Karamjeet, Confer Anthony W., and Murphy, George L., “Genetic and Immunologic Analyses of PlpE, a Lipoprotein Important in Complement-Mediated Killing of *Pasteurella haemolytica* Serotype 1.” Infection and Immunity, Dec. 1998, vol. 66, No. 12, p. 5613-5619.

Morton, DVM, PhD, Rebecaa J., Panciera, DVM, PhD, Roger J., Fulton, DVM, PhD, Robert W., Frank, DVM, PhD, Glynn H., Ewing, DVM, PhD, Sidney A., Homer, PhD, John T., Confer, DVM, PhD, Anthony W., “Vaccination of cattle with outer membrane protein-enriched fractions of *Pasteurella haemolytica* and resistance against experimental challenge exposure.” *Am J Vet Res*, vol. 56, No. 7, Jul. 1995, pp. 875-879.

Pandher, Karamjeet, Murphy, George L., Confer, Anthony W., “Identification of immunogenic, surface-exposed outer membrane proteins of *Pasteurella haemolytica* serotype 1.” *Veterinary Microbiology* 65 (1999) pp. 215-226.

PCT International Search Report issued in connection with PCT/US03/34574, date of Mailing Jun. 18, 2004.

Confer, Anthony W., Ayalew, Sahlu, Panciera, Roger J., Montelongo, Marie, Whitworth, Lisa C., Hammer, Jordan D., “Immunogenicity of recombinant *Mannheimia haemolytica* serotype 1 outer membrane protein PlpE and augmentation of a commercial vaccine.” *Vaccine* 21 (2003) pp. 2821-2829 (published *after* priority date).

*Primary Examiner*—S. Devi
(74) *Attorney, Agent, or Firm*—Fellers, Snider, Blankenship, Bailey & Tippens

(57) ABSTRACT

Vaccines and methods against *M. haemolytica* infections in cattle. The vaccine compositions include a recombinant outer membrane protein of *M. haemolytica* designated PlpE and/or subunits thereof, alone or in combination with other antigenic components, and a carrier or diluent. The methods involve administering an effective immunizing amount of the vaccines to susceptible bovine.

3 Claims, 6 Drawing Sheets

Anti-PlpE:Commercial *M. haemolytica* Vaccines - Exp. 2

*M. HAEMOLYTICA* OUTER MEMBRANE PROTEIN P1PE AS A VACCINE OR VACCINE COMPONENT AGAINST SHIPPING FEVER

CROSS REFERENCE TO RELATED APPLICATION

This application is a divisional of U.S. patent application Ser. No. 10/696,544, filed Oct. 29, 2003, now abandoned, which application claims the benefit of U.S. Provisional Patent Application Ser. No. 60/422,305, filed Oct. 30, 2002, both of which applications are incorporated herein by reference.

STATEMENT REGARDING FEDERALLY SPONSORED RESEARCH

This invention was supported in part by the U.S. Government. The U.S. Government has certain rights in the invention as provided for by the terms of Grant Nos. 95-37204-1999 and/or 2002-02232 awarded by USDA-CSREES under the National Research Initiative Competitive Grants Program.

BACKGROUND OF THE INVENTION

1. Technical Field

The present invention relates generally to the prevention of bovine respiratory disease (BRD) and, in particular, its most severe form, termed “shipping fever”. More specifically, the present invention relates to the use of *M. haemolytica* outer membrane protein PlpE and subunits thereof as a vaccine or vaccine component against shipping fever.

2. Background

BRD is the major cause of beef cattle morbidity and mortality and of economic losses to the beef cattle industry. The cost of BRD to beef cattle producers approaches $1 billion annually.

BRD arises from the interaction of numerous contributing factors including physical stresses associated with weaning, shipment, inclement weather, and overcrowding coupled with viral and bacterial infections. The end result in severe cases is colonization of the lungs with pathogenic bacteria resulting in severe pneumonia. *Pasteurella multocida, Haemophilus somnus* and *Mannheimia* (formerly *Pasteurella*) *haemolytica* are associated with bovine pneumonia. However, *Mannheimia haemolytica* serotype 1 (S1) is by far the most important and commonly isolated bacterial pathogen in development of the often-fatal fibrinous pleuropneumonia in beef cattle known as pneumonic pasteurellosis or shipping fever.

Prevention and control of shipping fever in feedlots is attempted through three means: antibiotic treatment upon arrival of cattle at the feedlot, antibiotic therapy for sick cattle, and vaccination against BRD viruses and *M. haemolytica*. The extensive use of antibiotics to control shipping fever increases the possibility of antibiotic residues in meat and the development of drug-resistant bacteria in cattle, including those bacteria with potential impact on human health such as *Salmonella* and *E. coli* O157:H7.

Viral and bacterial vaccines for the control of shipping fever have been used for many years. Despite their availability, the disease continues to be a major bovine health problem. Because of the economic constraints of the cattle industry, bovine vaccines must be low in cost. Therefore, current *M. haemolytica* vaccines are crude, usually consisting of a culture supernatant, which contains *M. haemolytica* leukotoxin and sloughed surface proteins, and/or the killed bacterium. Perino and Hunsaker reviewed published field studies on commercial *M. haemolytica* vaccines and found that efficacy could be established in only 50% of the trials. (Bov Practitioner 1997; 31: 59–66) Thus, there is a continuing need that *M. haemolytica* vaccines be improved.

Immunity against *M. haemolytica* is thought to be primarily through production of serum antibodies that neutralize the secreted leukotoxin (LKT) and antibodies against surface antigens. The specific surface antigens that are important in stimulating host immunity to *M. haemolytica* are not known; however, several studies point towards the importance of outer membrane proteins (OMPs). Pandher et al. demonstrated 21 surface-exposed immunogenic outer membrane proteins in *M. haemolytica* S1 using protease treatment and Western blotting. (Pandher K, Murphy G L, Confer A W. *Identification of immunogenic, surface-exposed outer membrane proteins of Pasteurella haemolytica serotype* 1. Vet Microbiol 1999; 65: 215–26) High antibody responses to outer membranes, as measured by ELISA, and to several specific OMPs, as measured by quantitative Western Blotting, consistently correlated with resistance to challenge with virulent *M. haemolytica* S1 (Confer A W, McCraw R D, Durham J A, Morton R J, Panciera R J. *Serum antibody responses of cattle to iron-regulated outer membrane proteins of Pasteurella haemolytica A*1. Vet Immunol Immunopathol 1995; 47:101–10 and Mosier D A, Simons K R, Confer A W, Panciera R J, Clinkenbeard K D. *Pasteurella haemolytica antigens associated with resistance to pneumonic pasteurellosis.* Infect Immun 1989; 57:711–6). Vaccination of cattle with OMP-enriched cellular fractions, from *M. haemolytica* S1 significantly enhanced resistance of cattle against experimental challenge in the absence of antibodies to LKT. (Morton R J, Panciera R J, Fulton R W, Frank G H, Ewing S A, Homer J T, Confer A W. *Vaccination of cattle with outer membrane protein-enriched fractions of Pasteurella haemolytica and resistance against experimental challenge exposure.* Am J Vet Res 1995; 56: 875–879) However, the extraction procedure for bacterial outer membranes is time consuming and expensive, making use of purified OMPs as a component of a *M. haemolytica* vaccine impractical due to cost. Thus, it can be appreciated that the identification of specific, surface exposed immunogenic *M. haemolytica* OMPs that would stimulate strong antibody responses is highly desirable. Cloning and expression of the appropriate gene(s) and production of recombinant OMP could be achieved inexpensively.

One of the *M. haemolytica* OMP to which high antibody responses correlated with resistance against experimental challenge is a major 45 kDa OMP. Prior studies were undertaken to clone and characterize that protein. In 1998, Pandher et al. reported the cloning, sequencing and characterization of the gene for the major 45-kDa *M. haemolytica* S1 outer membrane lipoprotein, designated PlpE. (Pandher K, Confer A W, Murphy G L. *Genetic and immunologic analyses of PlpE, a lipoprotein important in complement-mediated killing of Pasteurella haemolytica serotype* 1. Infect Immun 1998; 66: 5613–9, which publication is incorporated herein by reference) PlpE was found genetically to have 32–35% similarity to an immunogenic lipoprotein, OmlA, demonstrated in *Actinobacillus pleuropneumoniae* serotypes 1 and 5. Affinity-purified, anti-PlpE antibodies recognized an OMP in all serotypes of *M. haemolytica* except in serotype 11. In addition, PlpE was determined to be surface-exposed, and in complement-mediated killing assays, a significant reduction was observed in killing of *M.*

*haemolytica* when bovine immune serum that was depleted of anti-PlpE antibodies was used as the source of antibody, suggesting that antibodies against PlpE may contribute to host defense against the bacterium.

It was the object, then, of the present invention to investigate the immunogenicity of recombinant PlpE and the potential for augmentation of existing vaccines to enhance protection against shipping fever.

SUMMARY OF THE INVENTION

In connection with the present invention, the gene for *M. haemolytica* outer membrane protein PlpE was cloned and the recombinant PlpE (rPlpE) was purified and used in immunological and vaccination studies. It was discovered that adjuvanted rPlpE was highly immunogenic in cattle, and vaccination of cattle with 100 μg of rPlpE markedly enhanced resistance against experimental challenge with virulent *M. haemolytica*. It was also discovered that the addition of rPlpE to a commercial *M. haemolytica* vaccine significantly enhanced ($p<0.05$) protection afforded by the vaccine against experimental challenge.

Thus, in one aspect of the present invention there are provided vaccine compositions comprising rPlpE or conservatively modified variants thereof separately or which may optionally be combined with adjuvant to enhance the protection efficacy of vaccine preparations against BRD and/or shipping fever, wherein the vaccine composition further comprises a pharmaceutically acceptable carrier or diluent. The rPlpE also may optionally be combined with other immunogens and/or existing commercially available vaccines to form a augmented vaccine composition, wherein the vaccine composition further comprises a pharmaceutically acceptable carrier or diluent and adjuvant.

In another aspect of the invention there are provided methods for inducing an immune response in cattle to provide immune protection against BRD and/or shipping fever, the method comprising administering to an at-risk animal an effective amount of a vaccine composition comprising rPlpE or conservatively modified variants thereof alone or in combination with an adjuvant and/or other immunogens to provide a means to reduce the risk of BRD, wherein the vaccine composition further comprises a pharmaceutically acceptable carrier or diluent.

Most of the structure of an OMP molecule would play no significant role in inducing protective immune responses, because extended portions of the molecule are buried, unexposed, in the outer membrane. Instead, immunity can be attributed to only short, surface-exposed epitopes of these proteins. Identification of such surface-exposed epitopes as protective antigens in animal models has been the target of peptide vaccine design strategies for various pathogenic bacteria. Because of *M. haemolytica* PlpE's potential as an important immunogen, we undertook these studies to characterize surface-exposed and immunologically important epitopes of PlpE and to produce and test recombinant epitopes corresponding thereto.

Thus, in another aspect of the invention there are provided immunologically important epitopes of rPlpE for use in vaccines and related methodologies.

A better understanding of the present invention, its several aspects, and its advantages will become apparent to those skilled in the art from the following detailed description, taken in conjunction with the attached figures, wherein there is described the preferred embodiment of the invention, simply by way of illustration of the best mode contemplated for carrying out the invention.

DETAILED DESCRIPTION OF THE INVENTION

Figure 1:
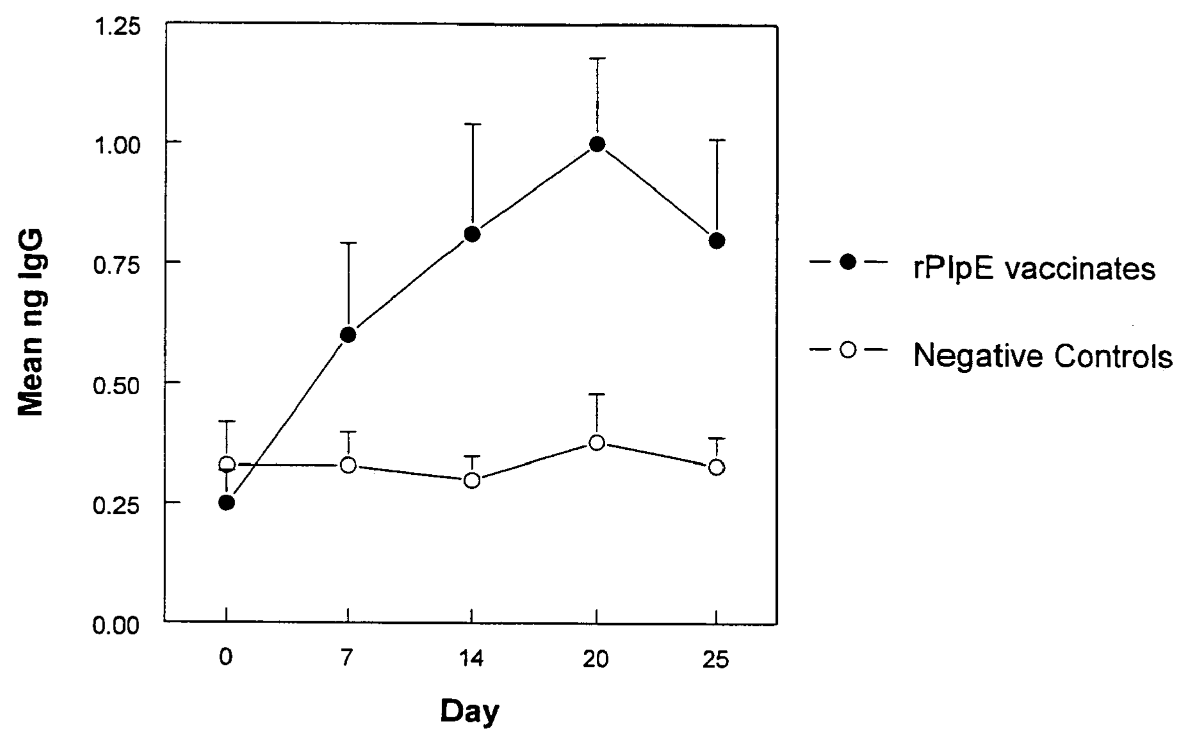
FIG. 1 is a graph depicting anti-PipE antibody response of 6 cattle vaccinated with 100 μg of rPlpE on day 0.

Before explaining the present invention in detail, it is important to understand that the invention is not limited in its application to the details of the embodiments and steps described herein. The invention is capable of other embodiments and of being practiced or carried out in a variety of ways. It is to be understood that the phraseology and terminology employed herein is for the purpose of description and not of limitation.

In accordance with the present invention there is provided a new vaccine against BRD and shipping fever through the use of discrete recombinant PlpE and subunits of rPlpE containing immunoprotective regions. In one aspect, only rPlpE or immunoprotective and functional regions thereof are utilized as the antigenic component of the vaccine. In another aspect, rPlpE or subunits thereof are utilized in combination with other antigen components, such as leukotoxin (LKT). Another aspect of the present invention relates to methods useful to reduce the risk of BRD and shipping fever in cattle and affect the biological transmission the disease among cattle populations.

The experiments described and non-limiting examples provided hereinafter demonstrate that cattle immunized with rPlpE and/or epitopes thereof are unexpectedly better protected against infection than cattle immunized with existing commercially available vaccines.

EXAMPLE 1

Immunogenicity of rPlpE and Vaccine Preparation

Studies were undertaken to determine the immunogenicity of outer membrane lipoprotein PlpE from *M. haemolytica* S1, determine if commercial vaccines stimulate antibodies to it, and examine if addition of recombinant PlpE to a commercial *M. haemolytica* vaccine would augment vaccine-induced immunity.

1. Materials and Methods 1.1. Bacterial Culture.

*M. haemolytica* S1 Oklahoma Strain was used for serology antigen preparation and for challenge of animals. Frozen stock cultures were plated onto brain-heart infusion (BHI) and grown at 37° C. in a 5% $CO_2$ environment for 18 hours. An isolated colony from each was propagated in 10 ml BHI broth with rotatory shaking at 120 oscillations/min. for 18 hours at 37° C. One hundred μl of suspension was added to 1 L of BHI broth and grown overnight. The bacteria were sedimented by centrifugation at 6000×g for 15 minutes, washed in 125 ml sterile phosphate buffered saline (PBS) and re-centrifuged as above 6000×g for 15 minutes. The bacteria were re-suspended in PBS and adjusted spectrophotometrically to a final concentration of approximately $1.0\times10^9$ CFU/ml (optical density of $A_{600}$=0.65).

1.2. Cloning and Purification of PlpE

The truncated form of plpE lacking the sequence encoding the putative signal peptide was amplified from pB4522 (Pandher et. al., 1998, supra) with the help of a forward primer starting 58 nucleotides into the 5'-end and priming into the open reading frame of plpE and a reverse primer which is complementary to the 3'-end of the gene. The amplimer was cut with BamHI and HindIII and ligated into an expression vector, pRSETA, cut with the same restriction enzymes. Competent *E. coli* DH5α were transformed with the ligation mixture and transformants were plated on Luria-Bertani (LB) agar plates with 50 μg/ml of ampicillin. Transformants were screened and appropriate subclones were identified. Plasmid DNA isolated from such subclones was submitted to the Oklahoma State University Core Facility where the nucleotide sequence was determined by the ABI Model 3700 (BioSciences) automated DNA sequencing system (SEQ ID NO: 1). Once the nucleotide sequence of a representative subclone was compared to that deposited in the GenBank (AF059036), the recombinant plasmid was introduced into BL21(DE3)pLysS by transformation to express and purify rPlpE (SEQ ID NO: 2).

The expression of rPlpE was done according to the protocol recommended by the manufacturer of the vector and the expression host (Invitrogen, CA). Briefly, single colonies of BL21(DE3)pLysS harboring the truncated plpE in pRSETA, were inoculated into appropriate volumes of LB broth with 50 μg/ml ampicillin and 34 μg/ml chloramphenicol. The culture were incubated at 37° C. until $A_{600}$=0.5 was attained at which time the synthesis of the recombinant protein was induced by adding IPTG (1 mM final concentration) and the induction was continued for at least 3 hours. In order to purify rPlpE, the culture was harvested and lysed by sonication. The cellular debris was then removed by centrifugation and the recombinant protein was loaded onto an affinity column packed by PROBOND nickel-chelating resin that selectively binds recombinant proteins with 6 histidine residues (His-Tag) at either the N- or Carboxy-terminus. In this instance, the His-Tag is at the N-terminus. The recombinant protein bound to the resin was then eluted with either a low pH buffer or competition with imidazole. The purity of each preparation was determined by SDS-PAGE followed Coomassie stain and Western blot with murine anti-PlpE ascites fluid.

1.3. Serology

Antibodies to formalin-killed *M. haemolytica* whole bacterial cells (WC), to LKT, and to rPlpE were determined by enzyme-linked immunosorbent assays (ELISAs). For WC preparation, *M. haemolytica* S1 were prepared from a washed 24 hour culture by suspending cells in 0.4% formalinized saline at a concentration determined spectrophotometrically to be 1.850 $OD_{650}$. LKT was prepared from supernatant from a 3-hour culture of *M. haemolytica* S1 grown in RPMI-1640 medium at 37° C. in a shaking incubator. The LKT was partially purified by precipitation with 40–60% ammonium sulfate. The precipitate was resuspended in 3M guanidine containing 59 mM $NaHPO_4$ and 100 mM NaCl. By SDS-PAGE of the LKT preparation, one intensely staining band was identified at 105 kDa and confirmed to be LKT on a western blot using an anti-LKT monoclonal antibody. Leukotoxic activity was $10^4$ LKT Units per ml. The 2-keto-3-deoxyoctonate concentration was 7.5 μg per mg of protein.

Wells of 96-well microtiter plates were coated with WC at an optical density reading equivalent to $10^8$ CFU of a 24-hour culture, with LKT at 50 ng per well, or with rPlpE at 50 ng per well. Sera were diluted in PBS-Tween 20 containing 1% BSA. ELISA for detection of serum antibodies to PlpE was done in the first immunogenicity study using serum dilutions ranging from 1:400–1:819,200. Otherwise, sera were tested against various antigens at dilutions of 1:800 for WC, 1:1600 for LKT, and 1:1600 for rPlpE, which were in the linear range of established dilution curves. The extent of antibody binding was detected using a 1:400 dilution of horseradish peroxidase-conjugated, affinity purified rabbit anti-bovine IgG (Kirkegaard & Perry Laboratories, Gaithersburg, Md.). Antibody responses are expressed as ng of immunoglobulin binding based on a set of IgG standards on each plate.

1.4. Animals

A total of 82 normal healthy beef calves (Hereford or Angus/Hereford cross) of mixed sex were used. The calves were weaned at around 6–8 months of age. All calves were vaccinated with 7-way Clostridial vaccine and leptospiral vaccine, and treated with anthelmintic 30 days prior to the study. The calves received free choice native grass hay supplemented with grain ration throughout the study. All animal studies were done following using protocols approved the University Institutional Animal Care and Use Committee (Protocol #182).

1.5. Anti-PlpE Responses with *M. haemolytica* Vaccines

To determine if vaccination of cattle with commercial or experimental *M. haemolytica* vaccines stimulate anti-PlpE antibodies, two studies were done. The first experiment was a retrospective study using sera from 18 cattle from previous vaccine studies. Serum antibodies to PlpE were determined on samples from the day of vaccination (day 0) and from day 14. On day 0, three calves each were vaccinated subcutaneously with one of the following commercial vaccines: *P. haemolytica* Toxoid, BRSV-BVD-IBR-$PI_3$ Vaccine (PYRAMID™ 4/PRESPONSE®, Fort Dodge Laboratories), *P. haemolytica*-multocida Bacterin-Toxoid (PULMO-GUARD™ PH-M, Boehringer Ingelheim), *P. haemolytica*-multocida-*Salmonella typhimurium* Bacterin-Toxoid (POLY-BAC B® 1, Texas Vet Labs). Three calves were each vaccinated with 2 mg of an *M. haemolytica* outer membrane preparation in Freund's incomplete adjuvant or $10^9$ CFU of live *M. haemolytica*. In addition, sera were analyzed from three non-vaccinated calves that spontaneously seroconverted to *M. haemolytica* based on positive antibody responses to WC and LKT.

The second vaccine experiment was a prospective study designed to follow the anti-PlpE antibodies for 42 days after a single dose of a commercial *M. haemolytica* vaccine or rPlpE. Thirty calves were divided equally among 6 groups and vaccinated subcutaneously once each on day 0 with PRESPONSE®, *P. haemolytica* Bacterin-Toxoid (ONE SHOT™, Pfizer), an avirulent *M. haemolytica* culture (ONCE PMH®, Intervet), PULMO-GUARD™ PH-M, or 100 μg of rPlpE in commercial adjuvant (Pfizer). Five unvaccinated calves served as controls. Sera were obtained on days 0, 7, 14, 21, 28, and 42, and antibodies to WC, LKT and PlpE were determined.

1.6. Recombinant PlpE Immunogenicity Studies

To determine if rPlpE was immunogenic, one calf each was vaccinated once with either 10, 50, or 100 μg of rPlpE in a commercial proprietary adjuvant (Pfizer Inc, Lincoln, Nebr.). One calf remained as a non-vaccinated control. Sera were obtained 21 days after vaccination and evaluated for end-point antibody titers against rPlpE using serial 2-fold dilutions. Twenty-four days after the initial vaccination, each calf and a non-vaccinated calf were transthoracically challenged with $5.0\times10^9$ CFU of live *M. haemolytica* from an overnight culture in accordance with established procedures. Four days later, calves were humanely killed, and lung lesion scores determined on a 20-point scale.

In a second cattle experiment, 6 cattle were vaccinated with 100 μg of rPlpE in commercial adjuvant on day 0 and 6 calves remained as non-vaccinated controls. On day 21, all cattle were challenged intrathoracically with $1\times10^9$ CFU of virulent M. haemolytica. Calves were humanely killed on day 25, and lung lesion scores determined. Antibody responses against rPlpE and *M. haemolytica* WC were determined on days 0, 7, 14 and 21 after vaccination.

In a third cattle experiment, PRESPONSE® was obtained from the manufacturer, and 18 weanling beef steers were equally allocated among the following vaccine groups: Group 1—PRESPONSE, Group 2—PRESPONSE+100 μg PlpE, and Group 3—non-vaccinated. Cattle were vaccinated on day 0 with 2 ml of PRESPONSE (manufacturer's recommended dosage) or 2 ml of PRESPONSE mixed with 0.5 ml of PlpE (100 μg). Antibody responses to *M. haemolytica* WC, rPlpE or to LKT were determined by ELISA on days 0, 7, 15, and 23. On day 24, cattle in Groups 1, 2, & 3 were challenged transthoracically with $3.0\times10^9$ CFU of *M. haemolytica*. Four days later, calves were humanely killed, and lung lesion scores determined.

1.7. Statistical Analysis

Mean rectal temperatures, antibody responses and lesion scores among the various groups were compared by Students t tests. Mean rectal temperatures and antibody responses within groups were compared by paired t tests. Differences were considered significant when $p<0.05$. Linear regression analyses were done to determine if there was a significant correlation between antibody response and lesion score.

2. Results 2.1. Recombinant PlpE Immunogenicity

In the first immunogenicity experiment that determined end-point anti-rPlpE titers in response to various doses of rPlpE, serum from the non-vaccinated calf had an end-point antibody titer of 1:400 against rPlpE. Sera from the 10, 50, and 100 μg vaccinates had titers of 1:12,800, 1:25,600, and 1:25,600, respectively. Intrathoracic challenge of those calves with virulent *M. haemolytica* resulted in a lesion score of 15.5 (20 maximum severity) for the non-vaccinated control calf. Lesion scores for the 10, 50, and 100 μg-vaccinates were 4.5, 3.0, and 3.5 respectively.

In the second immunogenicity experiment, vaccination with rPlpE on day 0 stimulates a significant increase in antibodies to rPlpE and to *M. haemolytica* WC on day 7 (FIG. 1). Those responses continued to increase to a maximum on day 20 and declined insignificantly on day 25, whereas antibodies to rPlpE and to WC failed to increase for the nonvaccinated calves. Anti-LKT antibodies did not significantly increase for either the rPlpE-vaccinated or control groups (data not shown). Mean lesion scores (±standard deviation) after challenge were 7.0±3.8 for nonvaccinated controls and 4.1±3.0 for the rPlpE vaccinates, a 41.4% reduction in lesion scores. Those differences were significantly different at the level of $p=0.07$. When data from the first experiment were combined with these data, the mean lesion score for nonvaccinated controls was 8.2±4.7 and mean lesion score for PlpE vaccinates was 3.9±2.6 ($p<0.05$), a 52.1% reduction in lesion scores.

2.2. *M. haemolytica* Vaccines

Figure 2:
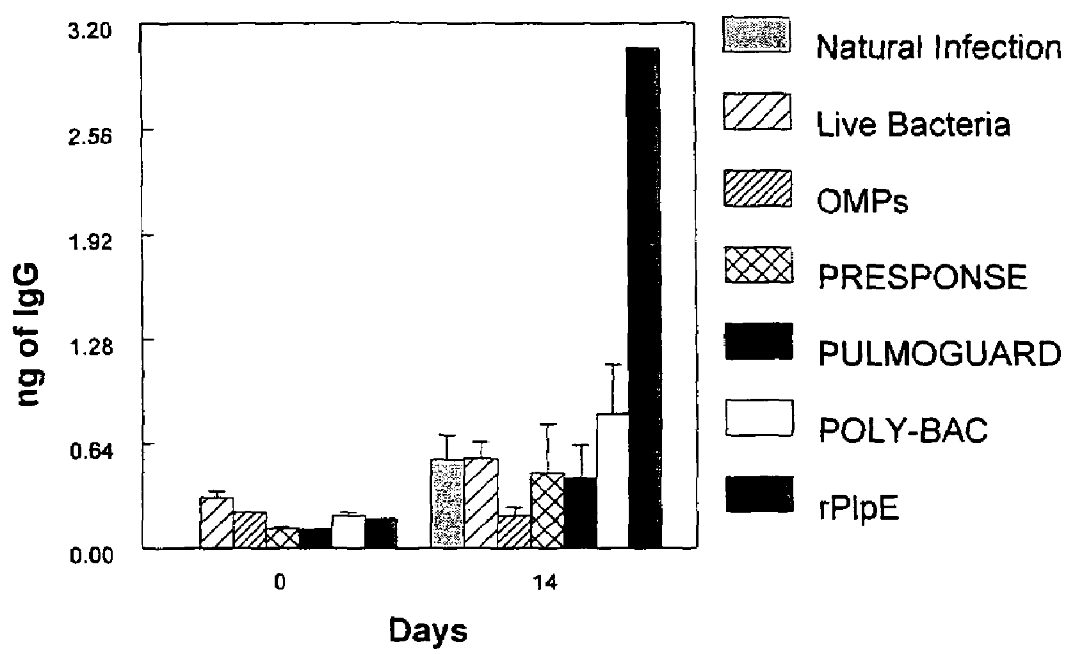
FIG. 2 is a bar graph depicting anti-PlpE antibody responses of cattle that spontaneously seroconverted to *M. haemolytica* (Natural Infection), vaccinated with commercial vaccines, *M. haemolytica* outer membranes (OMP), or live *M. haemolytica*.

In the first vaccine experiment, vaccination of calves with commercial vaccines, *M. haemolytica* outer membranes, and live *M. haemolytica* resulted in a nonsignificant increase in antibodies to PlpE (FIG. 2). In contrast, natural exposure to *M. haemolytica,* as indicated by spontaneous seroconversion, resulted in a significant increase in anti-PlpE antibodies. All vaccine-induced responses and natural exposure were substantially less than the antibodies produced in a calf vaccinated with 100 μg of rPlpE in commercial adjuvant. There were no significant differences among the antibody responses to rPlpE on day 14 for any of the commercial vaccine, live *M. haemolytica* vaccinated, or natural exposure groups. Antibody responses to *M. haemolytica* LKT and WC significantly increased for PULMOGUARD- and the live bacteria-vaccinated and natural exposure calves, whereas vaccination with outer membranes stimulated a significant antibody response to WC and vaccination with POLY-BAC and PRESPONSE failed to stimulate significant antibody responses to either *M. haemolytica* antigen (data not shown).

Figure 3:
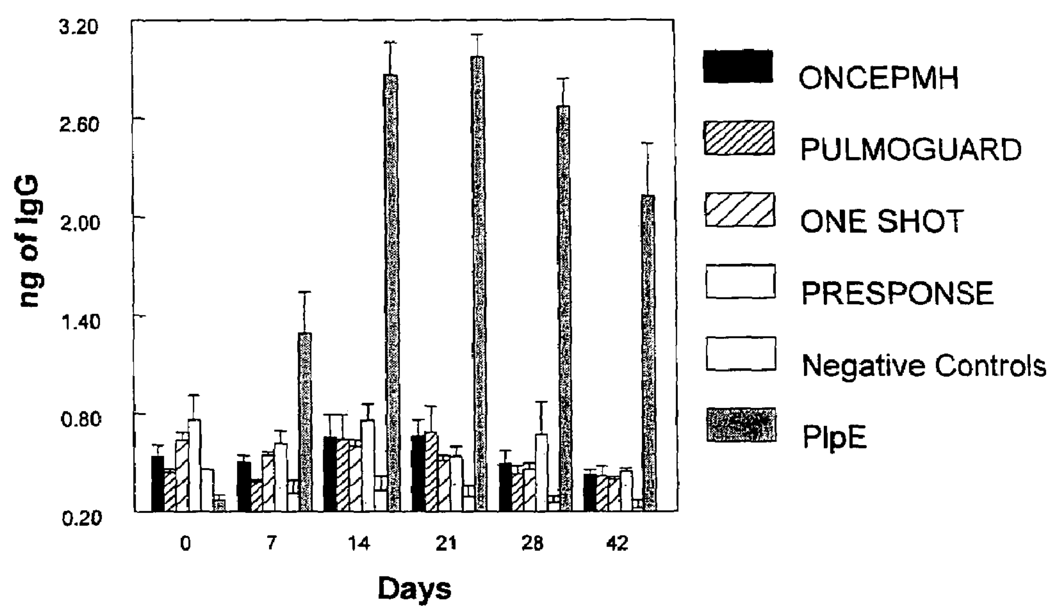
FIG. 3 is a bar graph depicting anti-PlpE antibodies for cattle vaccinated with commercial *M. haemolytica* vaccines or 100 μg of rPlpE.

In the second vaccine experiment, vaccination of calves with one of four commercial *M. haemolytica* vaccines resulted in nonsignificant increases in antibodies to PlpE (FIG. 3). Vaccination of calves with 100 μg of rPlpE in commercial adjuvant stimulated a significant increase in antibody responses to PlpE by day 7. That response continued to increase until it peaked on day 21 after vaccination. Vaccination with each commercial vaccine and with rPlpE resulted in significant increases in antibodies to *M. haemolytica* WC by day 7 (ONE SHOT and PRESPONSE) and by day 14 (ONCE PMH, PULMOGUARD, and rPlpE) (FIG. 2). Those responses remained significantly increased through day 14 (ONCE PMH and PRESPONSE) and day 42 (ONE SHOT, PULMOGUARD, and rPlpE). Peak antibody responses for ONE SHOT—vaccinated cattle were significantly greater than peak responses for ONCE PMH, PRESPONSE or rPlpE vaccinates. Although antibody responses to LKT increased after vaccination with each commercial vaccine, only the responses initiated by PULMOGUARD and ONE SHOT were significantly increased beginning on day 7 through day 28. Anti-LKT antibodies did not increase for the rPlpE vaccinates. Peak anti-LKT antibody responses for PULMOGUARD-vaccinated cattle were significantly greater than peak responses for ONCE PMH, PRESPONSE or rPlpE vaccinates, whereas peak anti-LKT antibody responses for ONE SHOT-vaccinated cattle were significantly greater than peak responses for PRESPONSE vaccinates.

2.3. Augmentation of Commercial Vaccine with rPlpE

Figure 4A:
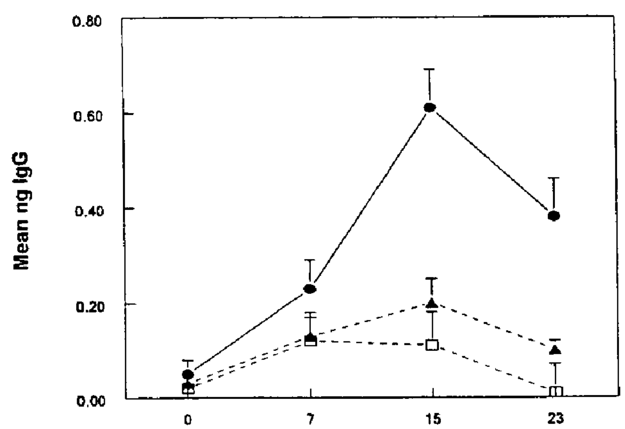
FIGS. 4A to 4C are a series of graphs depicting anti-PlpE (A), anti-*M. haemolytica* leukotoxin (B), and anti-*M. haemolytica* whole cells (C) in cattle vaccinated with PRESPONSE, PRESPONSE plus 100 μg of rPlpE, or nonvaccinated.
Figure 4B:
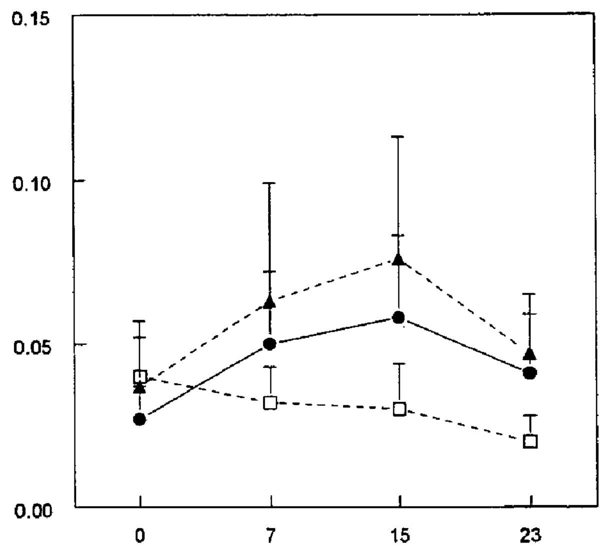
Figure 4C:
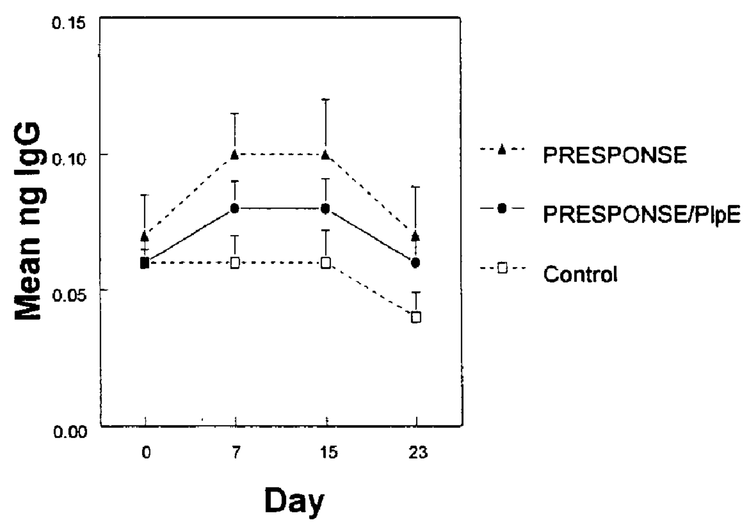

Because vaccination with commercial *M. haemolytica* vaccines stimulated low antibody responses to rPlpE, we investigated the augmentation of a commercial vaccine with rPlpE. Vaccination with PRESPONSE stimulated a significant increase in anti-rPlpE antibodies on day 15. Those responses, however, were not significantly different than were antibody responses of the nonvaccinated control calves on days 7, 15, and 23 (FIG. 4). PRESPONSE-rPlpE vaccination stimulated a significant increase in anti-rPlpE antibodies on days 7, 15 and 23, and those responses were significantly higher than responses for the PRESPONSE-vaccinated or nonvaccinated control calves. Anti-WC and anti-LKT responses were significantly increased on days 7 and 15 for the PRESPONSE- and PRESPONSE-rPlpE vaccinates. Those responses were not significantly different between those groups, whereas they were significantly greater than were anti-WC and anti-LKT antibody values for the nonvaccinated control group.

Figure 5:
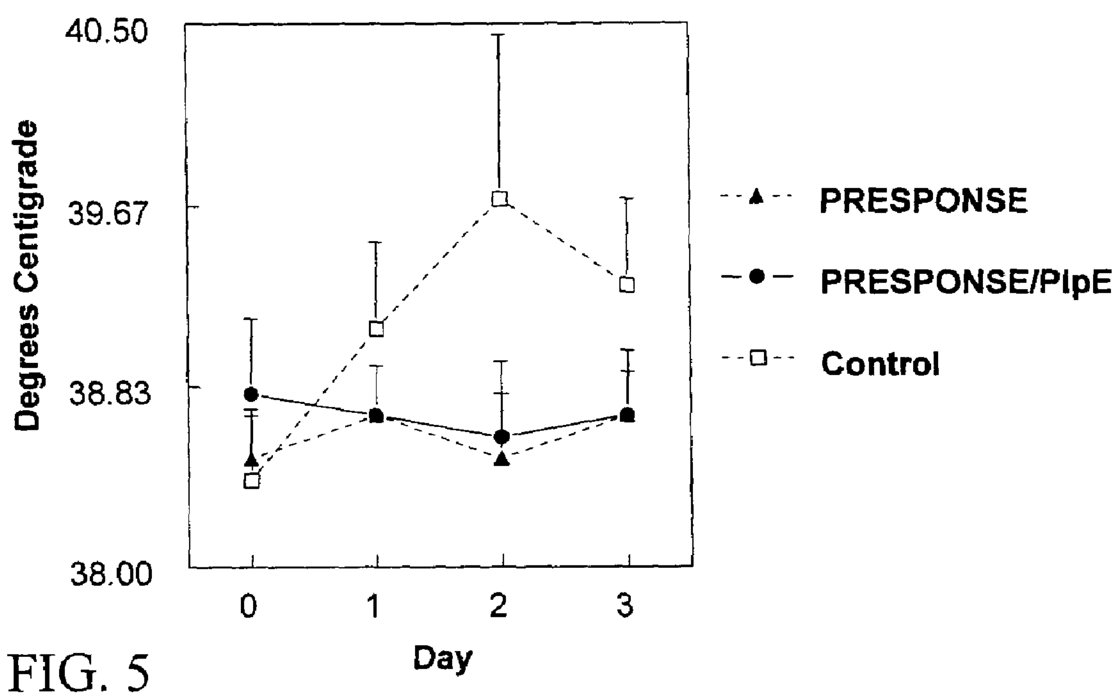
FIG. 5 is a graph depicting rectal temperatures of calves after challenge.

Rectal temperatures were taken on the day of challenge (day 24) and for the next 3 days (FIG. 5). Rectal temperatures remained essentially normal for all cattle except for the nonvaccinated Control group. In that group, rectal temperatures significantly increased on days 25 and 26, declining insignificantly on day 27. On days 26 and 27, mean rectal temperatures for the nonvaccinated Control group were significantly greater than for either the PRESPONSE or PRESPONSE/rPlpE groups. At necropsy, mean lung lesion scores were 7.9±3.6 for nonvaccinated controls, 3.0±1.3 for PRESPONSE-vaccinates (62.0% reduction in lesion score), and 1.1±0.9 for PRESPONSE/rPlpE vaccinates (86.1% reduction in lesion scores). Differences between the PRESPONSE and Control and PRESPONSE/PlpE and Control lesion scores were significant. In addition, mean lesion score for the PRESPONSE/PlpE group was significantly lower than for the PRESPONSE group. There was a significant correlation ($r=-0.598$, $p<0.01$) between high serum antibody responses to rPlpE at day 23 and low lesion scores.

3. Discussion

The foregoing studies demonstrate that rPlpE is highly immunogenic for cattle and that vaccination with rPlpE can greatly enhance resistance against experimental challenge with the bacterium. The in vivo studies definitively indicate that anti-PlpE antibodies can contribute to host defense against *M. haemolytica* infection.

Vaccination of cattle with commercial M. haemolytica vaccines, live *M. haemolytica* or outer membranes or after prior natural exposure stimulated low antibody responses to PlpE. For those vaccines, the rise in antibodies to rPlpE as measured on various days were not significant, and even those vaccines that stimulated high antibodies to *M. haemolytica* WC and LKT still stimulated low anti-rPlpE response. Commercial vaccine-induced anti-rPlpE antibody responses were substantially lower than those stimulated by vaccination with 100 μg of rPlpE in a commercial adjuvant. This was not unexpected, because commercial vaccines vary greatly in their composition in that some are composed of culture supernatants and bacterial cell components, others contain whole bacterial cells, and one is a live mutant. A somewhat surprising finding was that calves previously vaccinated with *M. haemolytica* outer membranes in Freund's incomplete adjuvant had low antibody responses to rPlpE on day 14 (see Morton et al., supra). Therefore, although PlpE is a major outer membrane protein, its concentrations in commercial and experimental vaccines are most likely low and variable. In addition, the adjuvant used may play an important role in stimulating antibodies to PlpE.

Because commercial vaccines stimulated low antibodies to PlpE, we used rPlpE to augment the antibody response of a commercial vaccine, PRESPONSE, and demonstrated that PRESPONSE/PlpE stimulated greater protection against challenge than did PRESPONSE alone. Conlon et al. previously demonstrated that addition of recombinant LKT enhanced the efficacy of a culture supernatant vaccine and decreased clinical signs and pneumonic lesions. (Conlon J A, Shewen P E, Lo R Y. *Efficacy of recombinant leukotoxin in protection against pneumonic challenge with live Pasteurella haemolytica* A1. Infect Immun 1991; 59: 587–91) Therefore, addition of one or more recombinant proteins to a *M. haemolytica* vaccine could be used by animal health companies to provide better products for protection of cattle against shipping fever.

In a recent survey, researchers found that of the *M. haemolytica* isolates from bovine respiratory disease from upper Midwestern United States were 60% A1, 26% A6 and 7% A2 with the remaining isolates from A9, A11 and untypable strains. (Al-Ghamdi G M, Ames T R, Baker J C, Walker R, Chase C C, Frank G H, Maheswaran S K. *Serotyping of Mannheimia* (*Pasteurella*) *haemolytica isolates from the upper Midwest United States.* J Vet Diagn Invest 2000; 12: 576–8) In another study, 60% of *M. haemolytica* isolates from cattle in a Texas feedyard were A1, whereas 40% were serotypes A2, A6, or A5 (Purdy C W, Raleigh R H, Collins J K, Watts J L, Straus D C. *Serotyping and enzyme characterization of Pasteurella haemolytica and Pasteurella multocida isolates recoveredfrom pneumonic lungs of stressedfeeder calves.* Curr Microbiol 1997; 34: 244–9) Therefore, although serotype 1 is the most common isolate from shipping fever, other serotypes play a role in the disease. Currently available *M. haemolytica* vaccines contain serotype 1 exclusively and therefore may or may not provide efficacious immunity against other serotypes. Cross serotype protection as stimulated by outer membrane vaccines or bacterins is limited. It is known that antibodies against *M. haemolytica* serotype1 LKT will cross neutralize the toxin prepared from other serotypes. Therefore, commercial vaccines that stimulate anti-LKT antibodies should provide some cross protection against other serotypes. However, Conlon et al. (supra) demonstrated that vaccination with recombinant LKT alone failed to stimulate protection against experimental *M. haemolytica* challenge, and Purdy et al (Purdy C W, Straus D C, Struck D, Foster G S. *Efficacy of Pasteurella haemolytica subunit antigens in a goat model of pasteurellosis.* Am J Vet Res 1993; 54:1637–47) found that vaccination of goats with LKT-impregnated agar beads stimulated incomplete immunity. Shewen and Wilkie (Shewen P E, Wilkie B N. *Vaccination of calves with leukotoxic culture supernatant from Pasteurella haemolytica.* Can J Vet Res 1988; 52:30–6) demonstrated that immunity to *M. haemolytica* was directed against both surface antigens and LKT. The actual surface antigen of importance in stimulating protection is not known for sure; however, studies indicate that it is most likely outer membrane proteins and not capsular polysaccharide or lipopolysaccharide. Pandher et al. (supra) demonstrated the presence of a PlpE—like protein in outer membranes of all *M. haemolytica* serotypes except serotype 11, an uncommon isolate from shipping fever. There was some variation in molecular masses among the various proteins. With the current findings, demonstrating immunogenicity of rPlpE and augmentation of a commercial vaccine that stimulates anti-LKT antibodies, the previous demonstration of a PlpE-like protein in most serotypes and that anti-LKT antibodies can neutralize LKT from other serotypes, the addition of rPlpE to a commercial vaccine that stimulates anti-LKT antibodies could enhance cross serotype protection in shipping fever.

EXAMPLE 2

Additional studies were undertaken to characterize surface-exposed and immunologically important epitopes of rPlpE.

1. Materials and Methods 1.1. Construction and Purification of Truncated Forms of rPlpE Three additional rPlpE proteins carrying varying degrees of deletions were constructed in pET28 and purified according to the method described above. The first of these was obtained by using plpBM-1 (5'-CTTGGATCCCAAGCACAAAATGTT-3') (SEQ ID NO: 3), a primer that primes 84 bp into the 5'end ofplpE thus introducing a deletion of 28 amino acids into the N-terminus end of rPlpE (rPlpEΔN28), the 2nd by plpBM-2 (5'-CCTGGATCCCAAGCAGAGGTTACT-3') (SEQ ID NO: 4), which primes 228 bp into the 5'end of plpE introducing a 76 amino acid deletion in the N-terminus of rPlpE (rPlpEΔN76), and the 3rd with plpBM-3 (5'-ATTGGATCCAATGCTGAACAACTC-3') (SEQ ID NO: 5) that primes 450 bp into 5'end of plpE introducing a deletion of 150 amino acids into the N-terminus in of rPlpE (rPlpEΔN150). The reverse primer in all instances was plpEER, (5'-GACTGAATTCTTATTTTTTCTCGCTAACCATTA-3') (SEQ ID NO: 6).

1.2. Production of Polyclonal Mouse Ascites

Three female, CFW mice were immunized 3 times with 50 μg of complete or truncated rPlpE diluted by half in RIBI (Corixa Corp, Seattle, Wash.) adjuvant. The first immunization was done subcutaneously (SC). Subsequent immunizations were done intraperitoneally (IP). A test-bleed was performed and the serum screened for antibodies to rPlpE by ELISA. The response was moderate, so two additional immunizations were performed IP. The mice were then injected with approximately $2\times10^6$ sarcoma cells (ATCC cat# TIB-66). Between 7 and 10 days after sarcoma injection, the mice started producing ascites. Ascites fluid was removed from each mouse three times; mice were then euthanized by barbiturate overdose.

1.3. Preparation of Affinity Columns and Purification of Anti-PlpE Antibodies

Purified rPlpE was coupled to NHS-activated Sepahrose 4 Fast Flow (Amersham Biosciences, Upsala, Sweden) according to the manufacturer's recommendation. Briefly, 3–7 mg of rPlpE in PBS was mixed with 2 ml bed volume of washed and equilibrated NHS-activated Sepharose 4 Fast Flow in an Econo Column (BioRad, Hercules, Calif.), incubated at 4° C. overnight at which time the non-reacted groups were blocked by 0.1 M Tris pH 8.0, and washed with alternating high and low pH buffers, Tris, pH 8.0 and acetate buffer pH 4.0, respectively. Several affinity columns were prepared with rPlpE carrying varying degrees of truncation from the N-terminus.

Anti-rPlpE antibodies against specific regions of PlpE were purified using the affinity columns described above. The ECONO-COLUMN with NHS-activated Sepharose coupled to an rPlpE of interest was fitted with a Flow adaptor according to the recommendation of the manufacturer (BioRad, Hercules, Calif.). The affinity column was equilibrated by applying Dulbecco's Phosphate Buffered Saline (DPBS) at a flow rate of 1 ml/min. Hyperimmune serum produced by immunizing calves with the intact rPlpE was mixed with DPBS in a ratio of 1 to 10 and passed through Nalgene 0.45 μm PES filters (Nalge, Rochester, N.Y.). The filtered serum was then applied to the equilibrated column via peristaltic pump at a flow rate of 1 ml/min. The flow thru was re-applied to the column several times to re-extract the serum by connecting the flow through to the reservoir of the initial serum. The column was then washed with DPBS. The complete removal of nonspecific proteins was determined with the help of the UV monitor attached to a chart recorder. Once there was no indication of nonspecific protein in the flow through, the specifically bound antibody was eluted with 100 mM Glycine Buffer (100 mM Glycine, 140 mM NaCl, pH 3.0) by collecting fractions in microfuge tubes containing 1/10 vol of 1 M Tris-HCl, pH 8.0. The absorbance of each fraction was determined at 280 nm. Those fractions that had a reading at least 2–3 times the background were pooled and dialyzed overnight against DPBS at 4° C. in a SLIDE-A-LYZER Dialysis Cassette (Pierce, Rockford, Ill.). The concentration of affinity purified antibody was determined with BCA Protein Assay Kit (Pierce, Rockford, Ill.). More specific antibodies against rPlpE with 28, 76 and 150 amino acids deletions on their N-termini, rPlpEΔN28 (pSAC63), rPlpEΔN76 (pSAC64) and rPlpEΔN150 (pSAC65), respectively, were purified as described.

Antibodies against regions of PlpE that are exposed on the surfaces of *M haemolytica* cells were purified as described by Turbyfill et al., (1998). Briefly, intact *M haemolytica* cells from the late log phase were incubated with hyperimmune bovine sera immunized by rPlpE or anti-PlpE mouse ascites diluted in PBS on ice for 2–4 hr with gentle agitation. The cells were spun down and washed several times with PBS. The antibodies bound to the surface were eluted by resuspending and agitating the cells in 0.1M Glycine, 140 mM NaCl, pH 3.0 for at least 30 minutes. The cells were centrifuged at 13,000×g, and the eluted antibodies were collected in the supernatant which was neutralized immediately by adding 1/10 volume of 1 M Tris, pH 8.0.

1.4. Epitope Mapping of PlpE by Peptide Array (Pepscan)

A peptide array comprising a total of 109 overlapping 13-mer peptides with 3 amino acid offsets was custom made by Sigma-Genosys LP (The Woodlands, Tex.). Briefly the synthesis of peptides was performed on cellulose membranes in which hydroxyl functions of a commercially available filter paper are derivatized with 9 fluorenylmethoxycarbonyl-B-alanine (Fmoc-B-Ala) with subsequent removal of the Fmoc group. The synthesis areas were defined by spotting a Fmoc-B-alanine-pentafluorophenyl ester solution to distinct areas on the membrane. Blocking the remaining amino functions between spots provided discrete reaction sites on the membrane for further standard solid phase peptide synthesis using amino acid pentafluorophenyl esters. Peptides remained covalently attached to the cellulose membrane by the C-terminus and have a free N-terminus.

The peptide array was probed with anti-PlpE hyperimmune sera as follows. Prior to blotting, membranes with the custom spots were blocked with SUPERBLOCK Dry Blend (Pierce, Rockford, Ill.) blocking buffer in TBS, pH 7.4. The membrane was then incubated in blocking buffer containing a primary antibody at a dilution of 1:1000 to 1:5000 for an hour. Following several washes with TBS, pH 7.4, supplemented with 0.05% TWEEN-20, 0.2% TRITON-X-100 (TBSTT), the membrane was incubated in SUPERBLOCK containing a goat anti-bovine or anti-mouse secondary antibody conjugated to Horse Radish Peroxidase (KPL, Gaithsburg, Md.) at dilutions 1:100,000 to 1:200,000 for one hour. The membrane was washed several times with TBSTT. The peptide array was incubated with SuperSignal West Pico Chemiluminescent Substrate working solution (0.125 ml/cm2) for 5 minutes, placed in plastic membrane protector and exposed to a CL-X Posure (Pierce, Rockford, Ill.) X-Ray film for varying durations of time. The X-Ray film was then developed in a KONICA SRX-101A Medical Film Processor (Taiwan). The developed X-Ray film was scanned by ARCUS 1200 AGFA scanner (Taiwan), and scanned images were analyzed using GENEPIX Pro 4.0 (Axon Instruments, Union City, Calif.). Signal intensities were defined as median pixel intensity following subtraction of local median background signal. The peptide array was stripped with RESTORE™ Western Blot Stripping Buffer (Pierce, Rockford, Ill.) according to the procedure recommended by the manufacturer before it was probed with a different anti-PlpE antibody. This was repeated several times with anti-PlpE antibodies obtained from different sources or purified in varieties of ways.

2. Results 2.1. Epitope Mapping of PlpE

The determination of the epitope map of PipE was attempted in two steps. The first approach involved the localization of the general area of immunogenic or immunodominant epitopes by deleting specific regions of PlpE from both the N-Terminus and C-Terminus by PCR with the help of specific primers. A total of 6 plasmid constructs carrying the plpE gene with varying degrees of deletions were made. The cloning of three of these constructs that carry deletions from the N-termini of PlpE, (pSAC63, pSAC64, and pSAC65) is described above. Three additional plasmids viz., pSAC30, pSAC31, and pSAC32 that carry 106(rPlpEΔC106), 96(rPlpEΔC96) and 86 (rPlpEΔC86) amino acid deletions on the C-terminus of PlpE, respectively, were designed and constructed. The reverse primers used to introduce these deletions on the 3'end of the plpE gene in the latter constructs were HNplp-1(5'-GATAAGCTTTTACCGTGCGGCAAATTC-3') (SEQ ID NO: 7), HNplp-2 (5'-AAAAAGCTTTTATTTAATTTCTACATC-3') (SEQ ID NO: 8), and HNplp-3 (5'-TTTAAGCTTTATATACTTCCTTGAGC-3') (SEQ ID NO: 9), respectively, and a forward primer plpEBH, (5'-GTCAGGATCCTGCGGAGGAAGCGGTAGC-3') (SEQ ID NO: 10). Amplimers were cut with BamHI and HindIII and cloned into pET28 or pRSETA cut with the same enzymes. Following confirmation of the identity of putative clones by both restriction analysis and sequencing, plasmids from true clones were introduced into BL21(DE3) by transformation where the truncated forms of PlpE were overexpressed and purified according to the protocol described earlier. The 6 truncated forms of rPlpE and the intact form were separated on a 12.5% SDS-PAGE for Western analysis. Hyperimmune serum from calves immunized with the intact rPlpE was used as primary antibodies and goat anti-bovine alkaline Phosphatase conjugated antibodies as secondary antibodies. Densitometric analysis of the respective bands in a Western blot in which the same amount of the recombinant proteins were loaded onto an SDS-PAGE and probed with hyperimmune serum from a calf that was immunized with rPlpE clearly showed that there are significant differences amongst recombinant proteins carrying deletions in the intensity of their reaction to the hyperimmune serum. Accordingly there is no difference in the intensity of binding between rPlpE and mutants with the deletions from the C-terminus viz., pSAC30, pSAC31, and pSAC32 that carry 106(rPlpEΔC106), 96(rPlpEΔC96) and 86 (rPlpEΔC86) amino acid deletions on the C-terminus of PlpE, respectively. The binding capacity of mutants carrying deletions on their N-termini decreases with increasing deletions. There is no appreciable difference between rPlpE and pSAC63 (rPlpEΔN28) with 28 amino acid deletions on the N-terminus. The reactivity of pSAC64 (rPlpEΔN76), which carries a deletion of 76 amino acids on the N-terminus, drops to 63%, which is a 37% loss in signal intensity, when compared to rPlpE. Further deletion into the N-terminus as seen in pSAC65 (rPlpEΔN150) reduces the binding capacity of the truncated proteins by 60%. These findings clearly suggest that the region between residues 28 and 76 from the N-terminus of PlpE carries a stretch of amino acids with possible epitope(s) that may be responsible for invoking the immune response elicited when rPlpE is used as a vaccine.

2.2. Fine Mapping of Epitopes on PlpE

Figure 6:
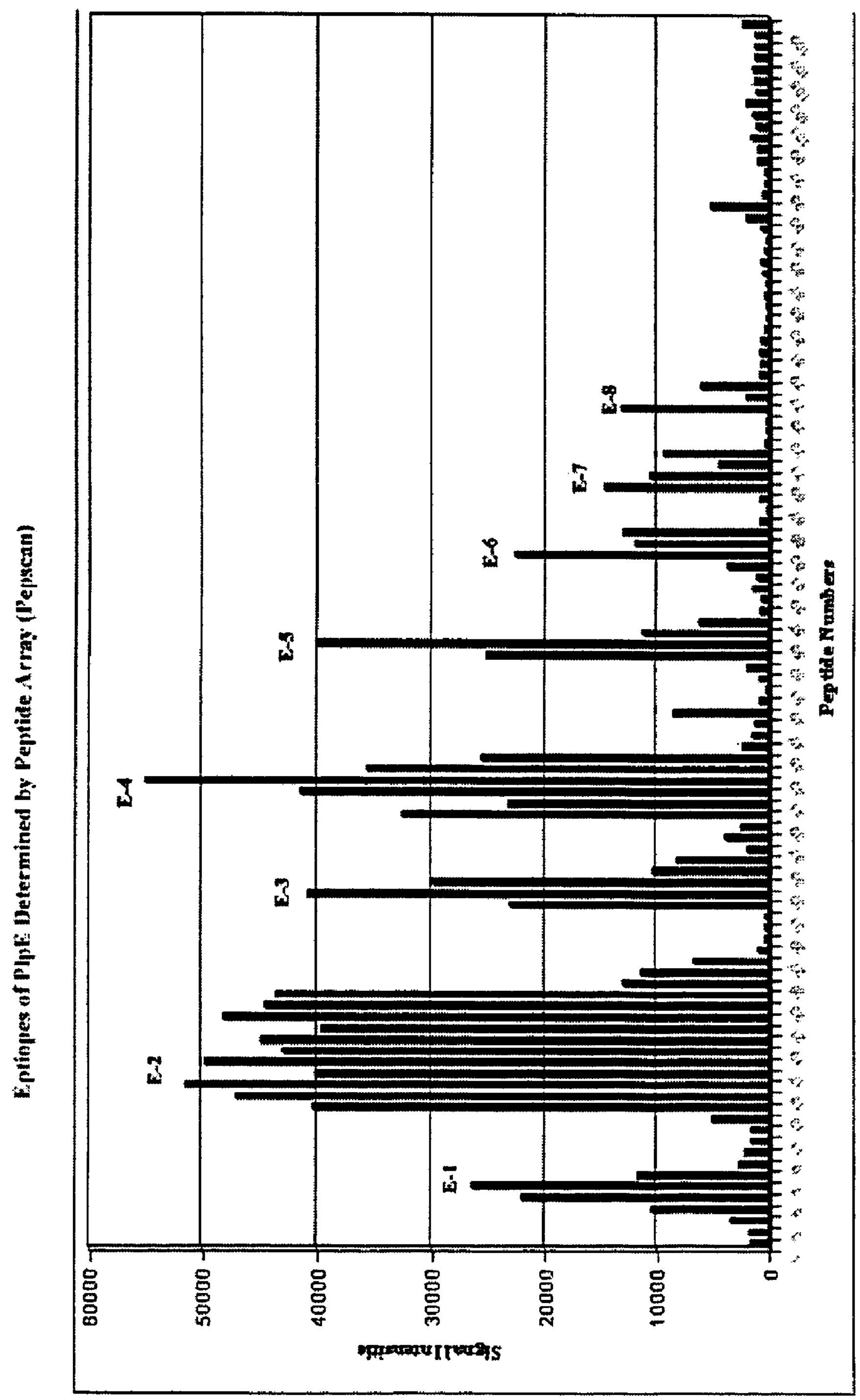
FIG. 6 is a graphical depicting of bovine antibody against surface exposed components of PlpE that was affinity purified with intact *M. haemolytica* cells and used to probe a peptide array. Densitometric analysis demonstrated a total of 8 distinct antigenic regions (E1–8) in PlpE with E2 being the largest and E4 having the highest densitometric signal.

Putative antigenic regions in PlpE were identified by using the MACVECTOR 7.0 software that employed algorithms such as antigenic index, hydrophilicity and surface probability. However, the identification of epitopes was done with a peptide array comprising 109 overlapping 13-mer peptides that were synthesized by the chemistry described earlier. The peptides were covalently bound to derivatized cellulose membrane by the C-terminus and have a free N-terminus. Anti-PlpE hyperimmune antibodies purified by any number of the methods described earlier were used to probe the peptide array. The custom spots were stripped and probed several times. When bovine antibody against surface exposed components of PipE that was affinity purified with intact *M. haemolytica* cells was used to probe the peptide array a total of 8 distinct regions (E1–8) were identified. (FIG. 6.) Epitope 1 (PNHPKPVLVPKTQNNL) (SEQ ID NO: 11) spans 3 peptides; epitope 2 (QNASQAQNAPQAQNAPQAQNAPQVENAPQAQNAPQVENAPQAE) (SEQ ID NO: 12), 11 peptides; epitope 3 (GSFDKIGSVKLNK) (SEQ ID NO: 13), 3 peptides; epitope 4 (KLGTPPKFDKVSGKKIIEE) (SEQ ID NO: 14), 6 peptides; epitope 5 (LIRRSDDLFYGYY) (SEQ ID NO: 15), 3 peptides; epitope 6 (ADKFSQYFVVYDE) (SEQ ID NO: 16), 3 peptides; epitope 7 (NISDKLTATYRKK) (SEQ ID NO: 17), 2 peptides; and epitope 8 (PHTKEFAARISKL) (SEQ ID NO: 18). More or less the same set of epitopes, albeit with decreasing intensities, were picked up when whole serum obtained from cows with a naturally high anti-PlpE antibody titer that were also challenged with live *M. haemolytica* was used. The signal intensities of all of the epitopes with the exception of epitope 2 were much lesser in this blot than in the earlier. The purification of IgG from the latter serum with Protein G affinity columns did not alter the above result in that exactly the same putative epitopes were identified suggesting that IgG was the class of immunoglobulins involved in this immune response. When whole hyperimmune serum from calves immunized with rPlpE was used to probe the stripped peptide array exactly the same set of peptides mentioned above were identified once again confirming the binding capacity of the above indicated stretches of amino acids along PlpE. On the other hand, when sera from calves that were given live *M. haemolytica* were used to probe the peptide array, epitope 2 was the only one that was picked up. According to the manufacturers of the custom spots, non-specific binding of the antibody-enzyme conjugate may occur to peptides that contain combinations of basic amino acids. When goat anti-bovine-HRP, the secondary antibody used in this project, was used to probe the spots, epitopes 1, 3, 4, 7, and 8 were picked up. The same sets of epitopes were identified when the array was probed with rabbit anti-bovine-HRP, showing putative epitopes 1, 3, 4, 7, and 8 were not true epitopes. In order to identify spots that would non-specifically bind bovine immunoglobulins, serum from colostrum deprived new born calf was used to probe the array. Interestingly, in addition to the putative epitopes identified by the secondary antibody-enzyme conjugates, i.e., 1, 3, 4, 7, and 8, epitopes 5, and 6 exhibited reactivity to bovine immunoglobulins. Epitope 2 was the only one that did not react to both the serum from the colostrums deprived calf and secondary antibody-enzyme conjugate showing that this epitope is the only one responsible for inducing the specific immune response when calves were either vaccinated with rPlpE or *M. haemolytica*.

A closer examination of epitope 2 shows that this is part of the region identified as having 8 imperfect repeats of hexapeptides (Pandher et. al., 1998). The 11 peptides (#13 through 23) identified here as epitope 2 comprise the last 4 residues of the $2^{nd}$ repeat described by Pandher et al., (1998) and the rest of the repeats i.e., repeats 3 through 8 with the exception of the $1^{st}$ hexapeptide. A feature of these 11 peptides is the lack of uniformity in their binding capacity as evidenced by the variation in their signal intensities. Peptides #15, 17, and 19 exhibit the highest signal intensities followed by #s 21 and 23. The first 4 residues of the N-termini of these peptides are Q, N, A and P, with the exception of #21 in which the first glutamine is replaced by glutamate. It is worthwhile noting that both glutamine and aspargine are positively charged, with hydrophobicity index of −0.91 and −0.92, respectively. The remaining 6 peptides in epitope 2 have proline at their N-termini instead of glutamine and this may account for their relatively lower signal intensity in the peptide array. The relatively high signal intensities exhibited by peptides 15, 17, and 19 may reflect the manner in which these epitopes are presented to the immune system under natural condition on the surfaces of *M. haemolytica* cells and the inherent immunogenic nature of these stretches of amino acids. The fact that epitope 2 contains significant number of prolines at defined intervals which are usually indicators of turns, has an unusually high number of very basic residues such as glutamine, aspargine and glutamate which are hydrophilic with high surface probability and 8 repeats are features that are usually associated with regions of protein that are associated with being immunogenic. Moreover, computer analysis of the deduced amino acid sequence of epitope 2 with algorithms such as Parker's antigenicity, Kyte/Doolittle hydrophilicity, surface probability and Chou Fasman □° structure indices show that the stretch of amino acids has a moderately high antigenicity, fairly hydrophilic, contains fairly high number of amino acids with very high surface probability and is characterized by series of turns associated with helices and sheets, respectively, all of which are strong indicators of a region that is potentially highly immunogenic.

Accordingly, it can be appreciated that subunits derived from PlpE, and especially epitope 2, are useful as well in the inventive vaccine compositions and methodologies. The inclusion of such region(s) enhances the host immune response directed against relevant immunoprotective epitopes.

It accordingly can be appreciated that the inventive vaccines utilize as distinct antigenic components rPlpE or subunits thereof capable of eliciting an antibody or other immune response against *M. haemolytica*. As a result, the invention encompasses proteins which may be the full length antigen, antigen fragment, antigen derivative or a fusion product of such antigen, antigen fragment or antigen derivative with another protein. Proteins included within the present invention include those depicted in the Sequence Listing as well as mutuants of said sequences capable of eliciting an antibody or other immune response which recognizes an epitope(s) of such amino acid sequences.

The nucleotide sequences used to generate the antigens may be inserted into any of a wide variety of expression vectors by a variety of procedures. Such procedures and others are deemed to be known by those skilled in the art. Suitable vectors include chromosomal, nonchromosomal and synthetic DNA sequences; e.g., derivatives of SV40; bacterial plasmids; phage DNAs; yeast plasmids; vectors derived from combinations of plasmids and phage DNAs, viral DNA such as baculovirus, vaccinia, adenovirus, fowl pox virus, pseudorabies, etc. The appropriate DNA sequence must be operatively linked in the vector to an appropriate expression control sequence(s) (promoter) to direct mRNA synthesis. As representative examples of such promoters, there may be mentioned LTR or SV40 promoter, the *E. coli* lac or trp, the phage lambda PL promoter and other promoters known to control expression of genes in prokaryotic and eukaryotic cells or their viruses. The expression vector also includes a non-coding sequence for a ribosome binding site for translation initiation and a transcription terminator. The vector may also include appropriate sequences for amplifying expression.

The vector containing an appropriate sequence, as well as an appropriate promoter or control sequence, may be employed to transform an appropriate host to permit the host to express the protein. Examples of host organisms and cells include bacterial strains (e.g., *E. coli, Pseudomonas, Bacillus, Salmonella,* etc.), fungi (e.g., yeasts and other fungi), animal or plant hosts (e.g., mouse, swine or animal and human tissue cells). The selection of the host is deemed to be within the scope of those skilled in the art.

As previously mentioned, it is also understood that the appropriate sequence present in the vector when introduced into a host may express part or only a portion of the protein which is encoded within the noted terminology, it being sufficient that the expressed protein be capable of eliciting an antibody or other immune response which recognizes an epitope(s) of the listed amino acid sequences.

The isolated polypeptides expressed by the host transformed by the vector may be harvested by methods which will occur to those skilled in the art and used in a vaccine for providing an enhanced immune response against infection with *M. haemolytica*. Vaccine preparation is easily accomplished using well known methods and techniques. An enhanced immune response is manifest by protection against infection or a decrease in severity of infection, which may be reflected in body temperature and antibody titers as described above.

The host expressing the antigen may itself be used to deliver antigen to non-human animals, by introducing killed or viable host cells that are capable of propagating in the animal. Direct incorporation of the nucleotide sequences into host cells may also be used to introduce the sequences into animal cells for expression of antigen in vivo.

Vaccine preparations are combined with physiologically acceptable carriers to form vaccines. The carrier employed in conjunction with vaccine may be any one of a wide variety of carriers. As representative examples of suitable carriers, there may be mentioned mineral oil, synthetic polymers, etc. Carriers for vaccines are well known in the art and the selection of a suitable carrier is deemed to be within the scope of those skilled in the art. The selection of a suitable carrier is also dependent upon the manner in which the vaccine is to be administered. The preferred physiologically acceptable carrier is an adjuvant.

Preferably, the inventive vaccine formulation is set to contain 10–100, and preferably about 100, micrograms of recombinant antigens in commercially available adjuvant (Pfizer).

The vaccines may be administered by a variety of routes including intravenously, intraperitoneally, intramuscularly, and subcutaneously. The preferred route of administration is subcutaneous. Alternatively, the vaccine may be administered intranasally or orally. The vaccine can be administered in a single dose or multiple doses until a protective effect is achieved.

In view of the above, it will be seen that the several objectives of the invention are achieved and other advantageous results attained. As various changes could be made in the above sequences, antigens, etc. without departing from the scope of the invention, it is intended that all matter contained in the above description or shown in the accompanying drawings shall be interpreted as illustrative and not in a limiting sense.

While the invention has been described with a certain degree of particularity, it is understood that the invention is not limited to the embodiment(s) set for herein for purposes of exemplification, but is to be limited only by the scope of the attached claim or claims, including the full range of equivalency to which each element thereof is entitled.

What is claimed is:

1. A method of inducing a protective immune response in an at-risk bovine animal against infection caused by *Mannheimia haemolytica* comprising administering to said bovine animal a vaccine composition comprising between 10 to about 100 micrograms of a purified recombinant PlpE outer membrane protein of *Mannheimia haemolytica* in a commercial adjuvant, wherein said purified recombinant PlpE comprises the amino acid sequence of SEQ ID NO: 2.

2. The method of claim 1, wherein the vaccine composition further comprises at least one other antigen of *Mannheimia haemolytica*.

3. The method of claim 1, wherein the vaccine composition comprises about 100 micrograms of said recombinant PlpE outer membrane protein.

* * * * *

UNITED STATES PATENT AND TRADEMARK OFFICE

CERTIFICATE OF CORRECTION

PATENT NO. : 7,144,580 B2
APPLICATION NO. : 11/235982
DATED : December 5, 2006
INVENTOR(S) : Confer et al.

It is certified that error appears in the above-identified patent and that said Letters Patent is hereby corrected as shown below:

Col. 1, line 21;
Replace “2002-02232” with --2002-35204-12250--

Signed and Sealed this

Twentieth Day of March, 2007

JON W. DUDAS
*Director of the United States Patent and Trademark Office*

SEQUENCE LISTING

```
<160> NUMBER OF SEQ ID NOS: 18

<210> SEQ ID NO 1
<211> LENGTH: 1310
<212> TYPE: DNA
<213> ORGANISM: Mannheimia haemolytica
<300> PUBLICATION INFORMATION:
<301> AUTHORS: Pandher et al.
<302> TITLE: Genetic and Immunologic Analyses of PlpE, a Lipoprotein
      Important in Complement-Mediated Killing of Pasteurella
      haemolytica Serotype 1
<303> JOURNAL: Infection and Immunity
<304> VOLUME: 66
<305> ISSUE: 12
<306> PAGES: 5613-5619
<307> DATE: 1998-12

<400> SEQUENCE: 1

agggctaatc tactacagcc ccaaaaattt tcataaggga aacgtttacg taaaactcct     60

cagaccactc attcttattt tatataaaaa atgtgataga cttctcgcag tttcgtttta    120

tatatttaag gaataactaa gtgaaattca ataaaaaatt aattttaaca tttgctgcaa    180

ccttagtttt aagtgcttgc ggaggaagcg gtagcggagg ttcgtcttca acaccgaatc    240

accccaaacc agtactagta ccaaaaacac aaaataatct tcaagcacaa aatgttcctc    300

aggcacaaaa tgcctctcag gcacaaaatg cccctcaggc acaaaatgct cctcaggcac    360

aaaatgctcc tcaggtggaa aatgctcctc aggcacaaaa tgctcctcag gtagaaaatg    420

ctcctcaagc agaggttact ccgcctgtac cacagccaca atcacaaaaa attgacggtt    480

cttttgataa aattggttca gtaaaactca ataaagaggc tcaaactctt gagcttagta    540

gattcacttt ggtggataaa ttaggcacac caccgaagtt tgataaagta agcggtaaaa    600

aaattattga agaaaaagat tttctcgtat taaatttgtc tgatattaat gctgaacaac    660

tctctggcga ttttcttatt cgccgtagcg atgatctatt ctatggctac tatcacgata    720

caaatggcaa aaatcttgtc gatgctgccg ataaattcag tcaatatttt gtcgtgtatg    780

atgagaaacg ggtaaatgat aatatctctg ataaattaac agcaacttac cgtaaaaaag    840

aaggctttgt atatggttca aatccacata ctaaagaatt tgccgcacgg atcagcaaat    900

tgggggatgt agaaattaaa tttgaaaatg gtcaagctca aggaagtata aaagacgaaa    960

aagatggaaa tgctgagatc tttactatta aaggtgatac aaaacagtta gagattaccc   1020

caacggaaag taaccgaatc attatagcaa ttttagacca aaatcaaaaa agctatactc   1080

caggaatgga aaaagcaatt atggaaacta agtttattga ttcaaaggct ggtaattccg   1140

accaaaaata cttaatcggt gaagcaaaaa gcgataactg gcaagcaata atggttagcg   1200
```

-continued

```
agaaaaaata aagttatctt ttgctaaaaa ctgaaataaa aaggctgagt ccgggtaata   1260

tcggcctcag tcttttaaat tgtagaaaat catctgtaga agatcaaacc              1310


<210> SEQ ID NO 2
<211> LENGTH: 337
<212> TYPE: PRT
<213> ORGANISM: Mannheimia haemolytica
<300> PUBLICATION INFORMATION:
<301> AUTHORS: Pandher et al.
<302> TITLE: Genetic and Immunologic Analyses of PlpE, a Lipoprotein
      Important in Complement-Mediated Killing of Pasteurella
      Haemolytica Serotype 1
<303> JOURNAL: Infection and Immunity
<304> VOLUME: 66
<305> ISSUE: 12
<306> PAGES: 5613-5619
<307> DATE: 1988-12

<400> SEQUENCE: 2

Cys Gly Gly Ser Gly Ser Gly Gly Ser Ser Ser Thr Pro Asn His Pro
1               5                   10                  15

Lys Pro Val Leu Val Pro Lys Thr Gln Asn Asn Leu Gln Ala Gln Asn
            20                  25                  30

Val Pro Gln Ala Gln Asn Ala Ser Gln Ala Gln Asn Ala Pro Gln Ala
        35                  40                  45

Gln Asn Ala Pro Gln Ala Gln Asn Ala Pro Gln Val Glu Asn Ala Pro
    50                  55                  60

Gln Ala Gln Asn Ala Pro Gln Val Glu Asn Ala Pro Gln Ala Glu Val
65                  70                  75                  80

Thr Pro Pro Val Pro Gln Pro Gln Ser Gln Lys Ile Asp Gly Ser Phe
                85                  90                  95

Asp Lys Ile Gly Ser Val Lys Leu Asn Lys Glu Ala Gln Thr Leu Glu
            100                 105                 110

Leu Ser Arg Phe Thr Leu Val Asp Lys Leu Gly Thr Pro Pro Lys Phe
        115                 120                 125

Asp Lys Val Ser Gly Lys Lys Ile Ile Glu Glu Lys Asp Phe Leu Val
    130                 135                 140

Leu Asn Leu Ser Asp Ile Asn Ala Glu Gln Leu Ser Gly Asp Phe Leu
145                 150                 155                 160

Ile Arg Arg Ser Asp Asp Leu Phe Tyr Gly Tyr Tyr His Asp Thr Asn
                165                 170                 175

Gly Lys Asn Leu Val Asp Ala Ala Asp Lys Phe Ser Gln Tyr Phe Val
            180                 185                 190

Val Tyr Asp Glu Lys Arg Val Asn Asp Asn Ile Ser Asp Lys Leu Thr
        195                 200                 205

Ala Thr Tyr Arg Lys Lys Glu Gly Phe Val Tyr Gly Ser Asn Pro His
    210                 215                 220

Thr Lys Glu Phe Ala Ala Arg Ile Ser Lys Leu Gly Asp Val Glu Ile
225                 230                 235                 240

Lys Phe Glu Asn Gly Gln Ala Gln Gly Ser Ile Lys Asp Glu Lys Asp
                245                 250                 255

Gly Asn Ala Glu Ile Phe Thr Ile Lys Gly Asp Thr Lys Gln Leu Glu
            260                 265                 270

Ile Thr Pro Thr Glu Ser Asn Arg Ile Ile Ile Ala Ile Leu Asp Gln
        275                 280                 285

Asn Gln Lys Ser Tyr Thr Pro Gly Met Glu Lys Ala Ile Met Glu Thr
    290                 295                 300
```

-continued

```
Lys Phe Ile Asp Ser Lys Ala Gly Asn Ser Asp Gln Lys Tyr Leu Ile
305                 310                 315                 320

Gly Glu Ala Lys Ser Asp Asn Trp Gln Ala Ile Met Val Ser Glu Lys
                325                 330                 335

Lys


<210> SEQ ID NO 3
<211> LENGTH: 24
<212> TYPE: DNA
<213> ORGANISM: Artificial
<220> FEATURE:
<223> OTHER INFORMATION: oligonucleotide primer

<400> SEQUENCE: 3

cttggatccc aagcacaaaa tgtt                                              24


<210> SEQ ID NO 4
<211> LENGTH: 24
<212> TYPE: DNA
<213> ORGANISM: Artificial
<220> FEATURE:
<223> OTHER INFORMATION: oligonucleotide primer

<400> SEQUENCE: 4

cctggatccc aagcagaggt tact                                              24


<210> SEQ ID NO 5
<211> LENGTH: 24
<212> TYPE: DNA
<213> ORGANISM: Artificial
<220> FEATURE:
<223> OTHER INFORMATION: oligonucleotide primer

<400> SEQUENCE: 5

attggatcca atgctgaaca actc                                              24


<210> SEQ ID NO 6
<211> LENGTH: 33
<212> TYPE: DNA
<213> ORGANISM: Artificial
<220> FEATURE:
<223> OTHER INFORMATION: oligonucleotide primer

<400> SEQUENCE: 6

gactgaattc ttattttttc tcgctaacca tta                                    33


<210> SEQ ID NO 7
<211> LENGTH: 27
<212> TYPE: DNA
<213> ORGANISM: Artificial
<220> FEATURE:
<223> OTHER INFORMATION: oligonucleotide primer

<400> SEQUENCE: 7

gataagcttt taccgtgcgg caaattc                                           27


<210> SEQ ID NO 8
<211> LENGTH: 27
<212> TYPE: DNA
<213> ORGANISM: Artificial
<220> FEATURE:
<223> OTHER INFORMATION: oligonucleotide primer

<400> SEQUENCE: 8

aaaaagcttt tatttaattt ctacatc                                           27
```

<210> SEQ ID NO 9
<211> LENGTH: 27
<212> TYPE: DNA
<213> ORGANISM: Artificial
<220> FEATURE:
<223> OTHER INFORMATION: oligonucleotide primer

<400> SEQUENCE: 9
tttaagcttt tatatacttc cttgagc 27

<210> SEQ ID NO 10
<211> LENGTH: 28
<212> TYPE: DNA
<213> ORGANISM: Artificial
<220> FEATURE:
<223> OTHER INFORMATION: oligonucleotide primer

<400> SEQUENCE: 10
gtcaggatcc tgcggaggaa gcggtagc 28

<210> SEQ ID NO 11
<211> LENGTH: 16
<212> TYPE: PRT
<213> ORGANISM: Mannheimia haemolytica

<400> SEQUENCE: 11

Pro Asn His Pro Lys Pro Val Leu Val Pro Lys Thr Gln Asn Asn Leu
1 5 10 15

<210> SEQ ID NO 12
<211> LENGTH: 43
<212> TYPE: PRT
<213> ORGANISM: Mannheimia haemolytica

<400> SEQUENCE: 12

Gln Asn Ala Ser Gln Ala Gln Asn Ala Pro Gln Ala Gln Asn Ala Pro
1 5 10 15

Gln Ala Gln Asn Ala Pro Gln Val Glu Asn Ala Pro Gln Ala Gln Asn
20 25 30

Ala Pro Gln Val Glu Asn Ala Pro Gln Ala Glu
35 40

<210> SEQ ID NO 13
<211> LENGTH: 13
<212> TYPE: PRT
<213> ORGANISM: Mannheimia haemolytica

<400> SEQUENCE: 13

Gly Ser Phe Asp Lys Ile Gly Ser Val Lys Leu Asn Lys
1 5 10

<210> SEQ ID NO 14
<211> LENGTH: 19
<212> TYPE: PRT
<213> ORGANISM: Mannheimia haemolytica

<400> SEQUENCE: 14

Lys Leu Gly Thr Pro Pro Lys Phe Asp Lys Val Ser Gly Lys Lys Ile
1 5 10 15

Ile Glu Glu

<210> SEQ ID NO 15

-continued

```
<211> LENGTH: 13
<212> TYPE: PRT
<213> ORGANISM: Mannheimia haemolytica

<400> SEQUENCE: 15

Leu Ile Arg Arg Ser Asp Asp Leu Phe Tyr Gly Tyr Tyr
1               5                   10


<210> SEQ ID NO 16
<211> LENGTH: 13
<212> TYPE: PRT
<213> ORGANISM: Mannheimia haemolytica

<400> SEQUENCE: 16

Ala Asp Lys Phe Ser Gln Tyr Phe Val Val Tyr Asp Glu
1               5                   10


<210> SEQ ID NO 17
<211> LENGTH: 13
<212> TYPE: PRT
<213> ORGANISM: Mannheimia haemolytica

<400> SEQUENCE: 17

Asn Ile Ser Asp Lys Leu Thr Ala Thr Tyr Arg Lys Lys
1               5                   10


<210> SEQ ID NO 18
<211> LENGTH: 13
<212> TYPE: PRT
<213> ORGANISM: Mannheimia haemolytica

<400> SEQUENCE: 18

Pro His Thr Lys Glu Phe Ala Ala Arg Ile Ser Lys Leu
1               5                   10
```